(12) United States Patent
Lee

(10) Patent No.: US 8,932,639 B2
(45) Date of Patent: *Jan. 13, 2015

(54) COMPOSITIONS COMPRISING SOLID PARTICLES ENCAPSULATED IN A CROSS-LINKED SILICONE MATRIX, AND METHODS OF MAKING THE SAME

(75) Inventor: Wilson A. Lee, Hauppauge, NY (US)

(73) Assignee: ELC Management LLC, Melville, NY (US)

( * ) Notice: Subject to any disclaimer, the term of this patent is extended or adjusted under 35 U.S.C. 154(b) by 138 days.

This patent is subject to a terminal disclaimer.

(21) Appl. No.: 13/544,297

(22) Filed: Jul. 9, 2012

(65) Prior Publication Data

US 2013/0177615 A1    Jul. 11, 2013

Related U.S. Application Data

(63) Continuation-in-part of application No. 12/538,455, filed on Aug. 10, 2009, now Pat. No. 8,246,997.

(60) Provisional application No. 61/093,882, filed on Sep. 3, 2008.

(51) Int. Cl.
```
A61K 9/50    (2006.01)
A61K 9/58    (2006.01)
A61K 9/14    (2006.01)
A61K 8/00    (2006.01)
A61K 8/11    (2006.01)
A61Q 17/04   (2006.01)
A61K 8/29    (2006.01)
A61K 8/893   (2006.01)
B01J 13/14   (2006.01)
B01J 13/22   (2006.01)
C09B 67/02   (2006.01)
A61K 8/27    (2006.01)
A61K 8/35    (2006.01)
A61K 8/81    (2006.01)
A61K 8/02    (2006.01)
C09B 67/08   (2006.01)
```

(52) U.S. Cl.
CPC . *A61K 8/11* (2013.01); *A61Q 17/04* (2013.01); *A61K 8/29* (2013.01); *A61K 8/893* (2013.01); *B01J 13/14* (2013.01); *B01J 13/22* (2013.01); *C09B 67/0097* (2013.01); *A61K 8/27* (2013.01); *A61K 8/35* (2013.01); *A61K 8/8164* (2013.01); *A61K 8/0241* (2013.01); *C09B 67/0013* (2013.01); *A61K 2800/412* (2013.01); *A61K 2800/63* (2013.01)
USPC ................ 424/497; 424/401; 424/59

(58) Field of Classification Search
USPC .................. 424/497, 401
See application file for complete search history.

(56) References Cited

U.S. PATENT DOCUMENTS

| | | |
|---|---|---|
| 3,865,759 A | 2/1975 | Smith |
| 5,182,173 A | 1/1993 | Swei |
| 5,502,144 A | 3/1996 | Kuo et al. |
| 5,744,126 A | 4/1998 | Horino et al. |
| 6,174,517 B1 | 1/2001 | Hansenne et al. |
| 6,660,281 B1 | 12/2003 | Nakanishi et al. |
| 7,135,206 B2 | 11/2006 | Schichtel |
| 8,246,997 B2 | 8/2012 | Lee |
| 2004/0091440 A1 | 5/2004 | Kamei et al. |
| 2005/0281770 A1 | 12/2005 | Elliott et al. |
| 2006/0222610 A1 | 10/2006 | Elliott |
| 2007/0183998 A1 | 8/2007 | Suzuki et al. |
| 2007/0196291 A1 | 8/2007 | Sakuta |
| 2008/0305338 A1 | 12/2008 | Mizutani et al. |
| 2010/0055139 A1 | 3/2010 | Lee |

FOREIGN PATENT DOCUMENTS

| | | |
|---|---|---|
| EP | 1065234 | 1/2001 |
| EP | 1541121 | 6/2005 |
| JP | H08-165433 | 6/1996 |
| JP | H09-2929 | 1/1997 |
| JP | 10-265357 | 10/1998 |
| JP | 2000-503677 | 3/2000 |
| JP | 2001-072891 | 3/2001 |
| JP | 2002-205911 | 7/2002 |
| JP | 2002-363445 | 12/2002 |
| JP | 2003-226812 | 8/2003 |
| JP | 2004-231609 | 8/2004 |
| JP | 2005-194271 | 7/2005 |
| JP | 2006-176557 | 7/2006 |
| JP | 2008-037846 | 2/2008 |
| KR | 10-2007-0114943 | 12/2007 |
| WO | WO98/13016 | 4/1998 |

OTHER PUBLICATIONS

PCT Int'l Search Report; Int'l Application No. PCT/US2013/049161; Completion Date: Sep. 5, 2013; Date of Mailing: Sep. 6, 2013.
PCT Written Opin of the Int'l Searching Authority; Int'l Application No. PCT/US2013/049161; Completion Date: Sep. 5, 2013; Date of Mailing: Sep. 6, 2013.
Pan, et al.; Adverse Effects of Titanium Dioxide Nanoparticles on Human Dermal Fibroblasts and How to Protect Cells; Small; www.small-journal.com; vol. 5; No. 4; pp. 511-520; 2009.
Lee, The Efficacy of Surface Modified Nano Titanium Dioxide Against Photocatalytic Activity From the Ultra Violet Irradiation; a Ph.D. Dissertation; Stony Brook University; vol. 69-01; pp. 1-61; May 2007.
PCT Int'l Search Report; Int'l Application No. PCT/US2009/053281; Completion Date: Mar. 22, 2010; Date of Mailing: Mar. 23, 2010.
PCT Written Opin of the Int'l Searching Auth; Int'l Application No. PCT/US2009/053281; Completion Date: Mar. 22, 2010; Mailing Date: Mar. 23, 2010.

*Primary Examiner* — Gina Justice
(74) *Attorney, Agent, or Firm* — Cynthia R. Miller

(57) ABSTRACT

The present invention relates to topical compositions containing solid particles that are stabilized via encapsulation into a cross-linked silicone matrix. The stabilized particles possess an electrical potential sufficient to prevent the particles from penetrating into the skin. The particles can readily be used either alone or in combination with other skin care actives to form topical compositions with improved stability and performance.

20 Claims, 1 Drawing Sheet

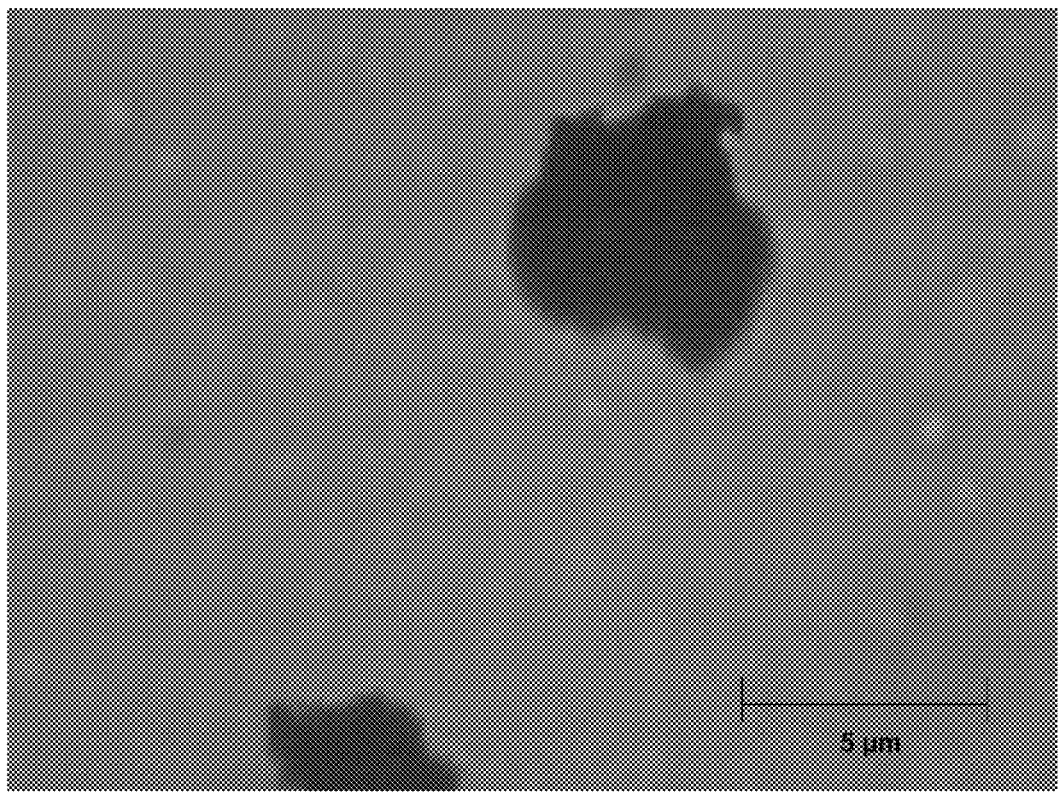

COMPOSITIONS COMPRISING SOLID PARTICLES ENCAPSULATED IN A CROSS-LINKED SILICONE MATRIX, AND METHODS OF MAKING THE SAME

This application is a continuation-in-part of application Ser. No. 12/538,455 filed Aug. 10, 2009 now U.S. Pat. No. 8,246,997, which claims priority of provisional application U.S. 61/093,882, filed Sep. 3, 2008.

FIELD OF THE INVENTION

The present invention relates to topical compositions comprising stabilized particulate components, as well as methods of making the same.

BACKGROUND OF THE INVENTION

Cosmetic or topical compositions typically comprise one or more particulate components, such as, for example, pigments or dyes, fillers, thickeners, sunscreen agents, and the like. Such particulate components are often insoluble in the respective solvent or carrier system and remain dispersed or suspended in the cosmetic or topical compositions.

However, whenever there are changes in the pH and temperature in the surrounding environment, the dispersed or suspended particles may agglomerate with one another and precipitate out of the composition. Furthermore, the smaller the particle size, the larger the active surface area, and the more susceptible such particulate components are toward adverse interactions or interference with other ingredients or components in the cosmetic or topical compositions, which may destabilize the cosmetic or topical compositions or reduce the overall performance thereof. Additionally, particulate components that are less than 40 nm in size can penetrate into the skin and lead to apoptosis.

There is therefore a continuing need for treating or modifying the particulate components of cosmetic or topical compositions in order to eliminate or mitigate the above-described drawbacks and improve the overall stability of the compositions without adversely affecting the chemical and physical properties of the particulate components.

There is also a need for improving the chemical and/or physical properties of the particulate components through surface treatment or modification.

SUMMARY OF THE INVENTION

In one aspect, the present invention relates to a topical composition comprising a dispersion of treated particles in a cosmetically or pharmaceutically acceptable carrier, wherein each of the treated particles comprises one or more core particles encapsulated in a cross-linked silicone matrix, and wherein each of the treated particles possesses an electrical potential in the range of from about −40 mV to about −80 mV.

In another aspect, the present invention relates to a treated particle comprising one or more titanium dioxide or zinc oxide core particles encapsulated in a cross-linked silicone matrix, while the treated particle has a particle size ranging from about 1 micron to about 50 microns and possesses an electrical potential in the range of from about −40 mV to about −80 mV.

In a still further aspect, the present invention relates to a method for forming treated particles, comprising:

(a) coating one or more core particles having an average particle size ranging from about 0.001 micron to about 0.5 micron with an anionic copolymer selected from the group consisting of acrylates copolymers and methyl vinyl ether and maleic anhydride (PVM/MA) copolymers, wherein the anionic copolymer possesses an electrical potential in the range of from about −10 mV to about −100 mV;

(b) coating the coated particles of (a) with silicone;

(c) contacting the coated particles of (b) with a cross-linking agent, wherein the cross-linking agent comprises a stannous carboxylate capable of effectuating cross-linking of the silicone coating, thereby forming a cross-linked structure with the core particles encapsulated therein; and (d) reducing the cross-linked structure into treated particles having an average particle size ranging from about 1 micron to about 50 microns and possessing an electrical potential ranging from about −40 mV to about −80 mV, wherein each of the treated particles comprises one or more of said core particles encapsulated in a cross-linked silicone matrix.

Other aspects and objectives of the present invention will become more apparent from the ensuing description, examples, and claims.

BRIEF DESCRIPTION OF THE DRAWING

The lone FIGURE is a microscope image of a treated particle formed by first coating $TiO_2$ core particles with silicone, then cross-linking the silicone coating to form a cross-linked structure, followed by milling/grinding of the cross-linked structure, according to one embodiment of the present invention.

DETAILED DESCRIPTION OF THE INVENTION

The present invention provides stabilized particulate components that are useful in cosmetic or topical compositions, as well as methods for stabilizing particulate components. Specifically, the treated particles, which are formed by encapsulating the particulate components in a cross-linked silicone matrix, are characterized by an average particle size that is at least 10 times, preferably 20 times, more preferably 50 times, and most preferably 100 times, larger than the average particle size of the initial particulate components. Each of the treated particles comprises a cross-linked silicone matrix encapsulating therein one or more core particles. Preferably, the physical and/or chemical properties of the entrapped core particles pertaining to or associated with their desired activities in the cosmetic or topical compositions are not adversely affected, while the significantly larger treated particles provide improved structural and spatial stability.

The core particles useful for the present invention can be any particulate components that are commonly used in cosmetic or pharmaceutical compositions, which include, but are not limited to: mineral pigments and fillers such as, for example, talc, kaolin, mica, bismuth oxychloride, chromium hydroxide, barium sulfate, polymethylmethacrylates (PMMA), boron nitride, nylon beads, polymeric powders (e.g., BPD 500 powders comprised of hexamethylene diisocyanate/trimethylol hexyllactone crosspolymer and silica that is commercially available from Kobo Products, Inc. at South Plainfield, N.J.), silica, silica beads, lakes (e.g., aluminum or calcium lake), metal oxides (e.g., black, yellow or blue iron oxide, chromium oxide, zinc oxide, and titanium dioxide), physical and chemical sunscreen agents, and any other organic and inorganic powders or particles. Preferably, but not necessarily, the core particles are comprised of a material capable of generating free oxygen radicals, and more preferably a metal oxide such as zinc oxide or titanium dioxide. The core particles can be of any regular or irregular shape, such as, for example, spherical, cubic, cylindrical, planar, fibrous, laminar, and the like.

The average particle size of the core particles as used in the present invention is preferably less than 1 micron, more preferably from about 0.001 micron to about 0.5 micron, and most preferably from about 0.01 to about 0.05 micron. A particularly preferred example of the core particles is a manganese modified titanium dioxide particle commercially available under the trade name of Optisol™ from Croda, Inc. at Edison, N.J. The core particle preferably constitutes about 10 to about 99 percent by weight of the treated particle, and more preferably, about 40 to 90 percent by weight of the treated particle.

Encapsulation of the core particles can be readily achieved in the present invention by first coating the core particles with silicone, then contacting the coated particles with a cross-linking agent comprising a stannous carboxylate capable of effectuating cross-linking of the silicone coating so as to form a cross-linked structure with the core particles encapsulated therein, and followed by reducing the cross-linked structure into treated particles of desired size.

The silicone as used in the present invention is preferably a silicone with branched reactive moieties. The term "branched reactive moieties" as used herein refers to side chain moieties that are branching off the polymeric backbone of the hydrophobic polymer and are capable of forming chemical bonds (which include, but are not limited to: van der Waals' bonds, hydrogen bonds, covalent bonds, and ionic bonds) with the surface of the core particle. The branched reactive moieties of the hydrophobic polymer of the present invention may include, but are not limited to: amino moieties, imino moieties, halogen moieties, hydroxyl moieties, and alkoxyl moieties. While not wishing to be bound by any particular theory, it is believed that the polyorganosiloxane backbone of the silicone forms a continuous coating over the core particles, while the branched reactive moieties of the silicone extend inwardly to the surface of the core particle and form a chemical bond with the core particle, thereby welding or anchoring the entire silicone coating onto the core particle.

In a particularly preferred, but not necessary, embodiment of the present invention, the silicone is a reactive ethoxy modified silicone with ethoxy or ethoxysilylethyl branched moieties, as described in U.S. Pat. No. 6,660,281, the content of which is incorporated herein by reference in its entirety for all purposes. Suitable reactive ethoxy modified silicones are commercially available under the trade names KF9901, KF9908, KF9909 or KP574 from Shin-Etsu Silicones of America, Inc., Akron, Ohio. Most preferably, the hydrophobic polymer of the present invention comprises a triethoxysilylethyl polydimethylsiloxyethyl hexyl dimethicone, which is commercially available under the trade name KF9909 from Shin-Etsu. The silicone is preferably present in an amount of about 0.01 to about 50 percent by total weight of the treated particle, and preferably, about 0.5 to about 15.0 percent by total weight of the treated particle.

The silicone as described hereinabove can be coated onto the core particles using any known coating technique, such as simple mixing, spray drying, fluid bed coating, and the like. Preferably, but not necessarily, the silicone is coated onto the core particles using techniques involving localized heat treatment, such as, for example, sonication achieved by using an Ultrasonic Processor, model # UPP-400A, Cycles: 20 KHz, available from Sonicor Instrument Corp., Copiague, N.Y. Typically, the core particles are provided in batches of from about 100 grams to about 1 kilogram, and each batch is mixed with a solution or dispersion of silicone. The mixture is then sonicated to form a silicone coating over the core particles in a period of time ranging from about 15 minutes to about 2 hours, and preferably from 10 minutes to about 1 hour. During the sonication, the branched reactive alkoxyl moieties of the silicone are energized and consequently form chemical bonds with the surface of the core particles, thereby cladding the polyorganosiloxane backbone of the silicone onto the surface of the core particles and forming a securely attached silicone coating thereover. After sonication, the silicone-coated particles are subjected to a centrifugation step whereby any residual silicone is removed from the batch of silicone-coated particles. Finally after centrifugation, the silicone-coated particles are dried by placing them in an oven for about 12 to 19 hours at a temperature at least sufficient to remove any residual water by evaporation (for example, about 100° C. to about 120° C.).

The silicone-coated particles as described hereinabove are then contacted with a cross-linking agent, which is preferably a stannous carboxylate capable of effectuating cross-linking of the silicone coating. Suitable stannous carboxylates that can be used as the cross-linking agent of the present invention include, but are not limited to stannous salts of linear or branched $C_8$-$C_{12}$ alkyl carboxylic acids, among which stannous octoate is the most preferred. Specifically, stannous octoate demonstrates in the present invention the capability of effectively cross-linking the silicone as described hereinabove at room temperature (i.e., 25° C.) upon continuous mixing for a period of time ranging from about 30 seconds to about 5 minutes, more preferably from about 45 seconds to about 2 minutes, and most preferably for about 1 minute.

The mixture is then allowed to sit for from about 1 minute to about 45 minutes, and a cross-linked structure is thereby formed with the core particles encapsulated therein. The cross-linked structure readily conforms to the shape of the container in which it is allowed to form. For example, if the mixture is poured onto a flat surface, the cross-linked structure will be formed into a flat sheet. For another example, if the mixture is poured into a cubic container, the cross-linked structure will be formed into a cube. The cross-linked structure so formed is typically a relatively solid structure.

Such cross-linked structure can be subsequently reduced into treated particles of desired average particle size by any suitable methods, such as crushing, grinding, pulverizing, milling, filtering, and the like. The resulting treated particles preferably have an average particle size ranging from about 1 micron to about 50 microns, more preferably from about 1 to about 15 microns, and most preferably from about 5 to about 8 microns, as determined by a Malvern Particle Size Analyzer, available from Malvern Instrument at Worcestershire, UK. The entrapped core particles may account for from about 10% to about 90% of the total weight of the resulting treated particles, more preferably 30% to about 75% of the total weight, and most preferably from about 40% to about 60% of the total weight. The cross-linked silicone may account for from about 5% to about 75% of the total weight of the resulting treated particles, more preferably from about 10% to about 60% of the total weight, and most preferably from about 30% to about 50% of the total weight. The FIGURE shows a microscopic view of a treated particle formed by the process described hereinabove, according to one embodiment of the present invention.

It is known that submicron particles, particularly those that are less than 40 nm in size, can penetrate or be engulfed into the skin cells and consequently lead to apoptosis. The inventor has discovered that one of the ways to prevent particles from penetrating into the cells is to modify the particles to have the same charge as the skin cells. Human skin and blood cells are known to be negatively charged, the skin cells possessing a negative charge of about −24 mV. The inventor has also found that when the particles possess an electrical potential which is at least 2.5 to 3 times the electrical potential of skin cells, a repulsive force between the particles and the skin is created. As a result, penetration of the particles into the cells can be prevented.

Therefore, in a preferred but not necessary embodiment of the present invention, the core particles are first coated with an inner layer of an anionic polymer before being encapsulated into the cross-linked silicone matrix. Specifically, the core particles are first coated with the anionic polymer and then with silicone followed by sonication, thereby forming coated particles that each comprises an inner coating of the anionic polymer and an outer coating of the silicone. Such coated particles are subsequently treated by cross-linking the outer silicone coating in the presence of a cross-linking agent as described hereinabove to form the cross-linked structure with the core particles encapsulated therein. The anionic polymer is believed to impart a negative charge to the overall treated particle.

For purposes of the present invention, any anionic polymer possessing an electrical potential ranging from about −10 mV to −100 mV, more preferably from about −30 mV to −80 mV, which will impart to the treated particle an electrical potential ranging from about −40 mV to −80 mV, more preferably from about −50 mV to −70 mV, can be used. It is important to select a polymer with a suitable electrical potential, because if the electrical potential of the treated particle is too low, the repulsion between the skin and the treated particles would be insufficient to prevent the particles from penetrating into the skin. On the other hand, if the electrical potential of the treated particles is too high, then the particles would not disperse properly when used in a composition. The electrical potential can be measured by diluting 0.1 part of the specimen in 30 parts of 99% ethanol and using a Zeta potential analyzer, such as the Zetasizer Nano available from Malvern Instruments Ltd, Worcestershire, UK. The Zeta potential is a measure of the magnitude of charge repulsion or attraction between particles.

While not wishing to be bound by any particular theory, it is believed that the particles of the present invention, possessing an electrical potential ranging from about −40 mV to −80 mV, such as those containing an inner layer of an anionic polymer, will not settle into the wrinkles or creases on the skin surface when situated on the surface of the skin due to the repulsive forces between the skin and the treated particles. For example, coating the surface of the particles (e.g. titanium dioxide) with 2% PVM/MA by total weight of the treated particles generates approximately −64 mV in a solvent system of water and/or alcohol. Thus, the two like charges of the skin cells and the particles repel one another, and this repulsive force can be measured.

Furthermore, the negative charge is trapped within the inner layer between the core particle and the outer cross-linked silicone matrix, and thereby becoming localized or immobilized around the core particle. As a result, a uniform negative charge is created around the entire particle. Although not wishing to be bound by any specific theory, the branched reactive alkoxyl moieties of the silicone in the outer matrix are believed to extend through the inner layer of the anionic polymer onto the surface of the core particle, preferably forming chemical bonds therewith to anchor the silicone layer as well as entrap the inner layer onto the core particle surface. The anionic polymer preferably has a higher density than the silicone but a lower density than the core particle. In this manner, the anionic polymer and the silicone can be sequentially coated onto the surface of the core particle, and the anionic polymer can be successfully entrapped between the core particle surface and the outer silicone layer. More preferably, a density difference of at least 0.01 g/cm$^3$ exists between the anionic polymer and the silicone so as to ensure the desired sequential deposition thereof.

Examples of suitable anionic polymers that can be used for forming the inner layer of the present invention include, but are not limited to, anionic copolymers such as acrylates copolymers and methyl vinyl ether and maleic anhydride (PVM/MA) copolymers. Acrylates copolymers include, but are not limited to, the Aculyn series of copolymers available from The Dow Chemical Company, Philadelphia, Pa. Preferably, the anionic polymer is a PVM/MA copolymer, which is commercially available as the Gantrez series of copolymers from International Specialty Products at Wayne, N.J. The Gantrez copolymers include, for example, Gantrez AN-119, Gantrez AN-139, Gantrez AN-149, Gantrez AN-169, Gantrez AN-903, and Gantrez S-97BF. The Gantrez copolymers are white, free-flowing powders that are initially insoluble in water, but they can be easily dispersed in water where the polymeric anhydride gradually hydrolyzes to produce a transparent solution of the free acid. All of the Gantrez copolymers contain methyl vinyl ether and maleic anhydride moieties but are differentiated from one another by molecular weights, which range widely from about 200,000 (for Gantrez AN-119) to about 2,000,000 (for Gantrez AN-179). More preferably, the anionic polymer used for forming the inner layer in the present invention comprises Gantrez AN-149 or Gantrez S-97BF. The inner layer may be present in an amount of about 0.2 to 5.0 percent by weight of the treated particle, and preferably, 0.5 to 2.0 percent by weight of the treated particle.

In another preferred but not necessary embodiment of the present invention, an active agent can be co-encapsulated with the core particles into the cross-linked silicone matrix, either with or without the inner layer of anionic polymer. The active agent is preferably a hydrophilic active agent including, but not limited to: water-soluble preservatives, carbohydrates, water-soluble vitamins, amino acids, antioxidants, and water-soluble extracts of biological materials. Examples of water-soluble extracts include but are not limited to, extracts from, artemia, phytosphingosine, polygonum cuspidatum root, yeast such as saccharomyces lysate, thermos thermophillus ferment, birch (*Betula alba*), mimosa tenuiflora (bark) extract, fruit, clove, rye, malt, corn, spelt, millet, barley, oat, wheat, sesame, cumin, turmeric, green onion, celery, ginseng, ginger, licorice, carrot, bupleurum root, *Ginkgo biloba* (gingko), *Foeniculi Fructus* (fennel), kiwi, berry such as *Moms bombycis* (mulberry), *Gentiana lutea* (gentian), algae such as red algae, *Arctium lappa* (burdock), *Salvia officinalis* (sage), *Lentinus edodes* (shiitake mushroom), *Perilla frutescens* (perilla), *Filipendula Multijuga, Fucus vesiculosis* (bladderwrack, sea weed), peach kernel, *Allium sativum* (garlic), *Poria cocos* (poria), *Humulus lupulus* (hops), *Mutan Cortex* (Moutan Bark), *Pimpinella major, Lactuca sative* (lettuce), *Astragalus membranaceous* (astragalus) and *Rosmarinus officinalis* (rosemary), *Prunus amygdalus* (almond), *Althea officinale* (althea), aloe, *Rosae Fructus* (rose fruit, or *Rosa multiflora*), *Scuttelaria baicalensis* (Huang qin), *Puerariae Radix* (*Pueraria* Root, or *Pueraria lobata*), chamomile such as *Chamomillae Flos* (German chamomile), *Gardenia jasminoides* (zhii zi, Gardeniae Fructus), *Sophora flavescens* Aiton (Sophorae Radix), *chlorella*, rice bran, *Paeoniae lactiflora* (white peony), ziyu (*Sanguisorba officinalis*, burnet), *Moms alba* (sang bai pi, mulberry), *Glycine max* (soybean), *Camellia sinensis* (tea), *Carthami Flos* (safflower), *Aesculus hippocastanum* (horse chestnut), *Melissa officinalis* (lemon balm) and Coicis Semen (*Coix lacryma-jobi* var. ma-yuen), *Angelica keisukei, Arnica montana* (arnica), *Foeniculum officinale* (fennel), *Isodon japonicus* Hara (*Isodonis Herba*), *Daucus Carota* (carrot), *Oryza sativa* (rice), *Crataegus cuneata* (Japanese howthorn), *Acorus calamus* (sweet flag), *Crataegus oxycantha* (howthorn), *Juniperus communis, Ligusticum wallichii* (Chinese lovage), *Swertiae Herba* (Swertia Herb), *Thymus vulgaris* (garden thyme), *Citrus reticulata* (*Citrus unshiu*), *Capsicum tincture, Angelicae sinensis* (angelica), *Aurantii Pericarpium* (bitter orange peel), *Ruscus aculeatus* (butcher's bloom), *Vitis vinifera* (grape), *Tilia japonica* (lime), *Citrus junos* and *Rosa canina* (rose hip), caffeine, *Cinnamomi Cortex* (cinnamon bark) and *Eriobotrya japonica* Lindl. (loquat), *Gambir, Echinacea, Phellodendri Cortex* (amur cork tree or *Phellodendron amurense*), *Hypericum perforatum* (St. John's wort), *Citrus sinensis* (orange), *Valeriana fauriei* Briquet, *Artemisia capillaris* Thunb., *Cucumis sativus* (cucumber), *Geranii Herba* (Geranium Herb), *Lithospermum erythrorhizon* Sieb. et Zucc., *Hedera helix, Achillea millefolium* (yarrow), *Ziziphus jujuba* (Chinese dates), *Calendula officinalis* (pot marigold), *Houttuynia cordata* (*Houttuyniae Herba, Houttuynia Herba*), *Potentilla erecta, Petroselinum crispum* (parsley), *Parietaria officinalis, Santalum album* (sandalwood), *Prunus persica* (peach), *Centaurea cyanus* (cornflower), *Eucalyptus globulus* (eucalyptus) and *Lavandula angustifolia* (lavender), *Persea americana* (avocado), *Nasturtium officinalis* (watercress), *Symphytum officinale* (comfrey), *Asarum sieboldii* (wild ginger), *Xanthoxyum piperitum* (Japan pepper), *Rehmannia glutinosa* (di huang), *Mentha piperita* (peppermint), *Syzygium aromaticum* (clove), *Tussilago farfara* (coltsfoot) and *Haematoxylum campechianum* (logwood); Oolong tea, *Cinchona succirubra* (peruvian bark), *Betula verrucosa* (birch) and *Glechoma hederacea* (ground ivy), milk and royal jelly, honey, cysteine and derivatives thereof, ascorbic acid and derivatives thereof, BHA, BHT, ferulic acid and derivatives thereof, grapeseed extract, pine bark extract, horseradish extract, hydroquinones, rosmarinic acid, coffee robusta seed, caffeic acid, tocopherol and derivatives thereof, green tea extract, sodium DNA, sodium ribonucleic acid, octyl, propyl and dodecyl gallates, uric acid and thiodiproprionate derivatives. The active agent, preferably, is an antioxidant or a natural water-soluble extract having antioxidant activities. More preferably, the active agent is a grape seed extract or a French maritime pine tree bark extract (also referred to as pycnogenol). The hydrophilic active agent can be present in the treated particle of the present invention in an amount of about 0.01 to 50.0 percent, and preferably, about 0.25 to 30.0 percent by weight of the treated particle.

The treated particles, according to one preferred embodiment, of the present invention as illustrated hereinabove can be readily formed, for example, by adding an anionic polymer and optionally a hydrophilic active agent, such as an antioxidant, into a specific solvent system to solubilize the anionic polymer and the hydrophilic active agent. The specific solvent system for practicing the present invention may contain a single solvent or a mixture of two or more solvents. Suitable solvents that can be used for forming such a solvent system include, but are not limited to: water, alcohols, and organic solvents, such as ethers, ketones, aliphatic hydrocarbons, halogenated hydrocarbons, and the like. Preferably, but not necessarily, the solvent system as used in the present invention is an aqueous solvent system containing water and optionally one or more alcohols. Core particles to be treated can then be added into the aqueous solution of anionic polymer and hydrophilic active agent and mixed until uniform. Subsequently, a silicone with branched reactive alkoxyl moieties is added into the aqueous solution, preferably with additional water and alcohol. The mixture is then sonicated for a sufficient period of time so as to form coated particles having an inner layer of anionic polymer and an optional hydrophilic active agent and an outer layer of hydrophobic polymer that are securely attached to the core particle, i.e., with little or no flaking-off. A cross-linking agent, e.g., stannous octoate, is then added into the solution at room temperature with continuous mixing. The resulting mixture is next poured into a container and allowed to sit for a sufficient period time to thereby forming a cross-linked structure, which is subsequently reduced to treated particles of desirable particle size by grinding, milling, crushing, pulverizing, filtering, and the like.

When formulated into topical compositions, the treated particles of the present invention provide various advantages and benefits that are not available in their un-encapsulated or "naked" counterparts. For example, because the core particles encapsulated in the cross-linked silicone matrix are sealed off from potentially destabilizing or degrading active ingredients in the topical composition, they are significantly more stable than their un-encapsulated or "naked" counterparts. Furthermore, if the core particles contain material or materials potentially capable of causing generation of reactive oxygen species (ROS), which may in turn degrade or otherwise interfere with other active ingredients in the topical composition, the encapsulation of such core particles in the cross-linked silicone matrix functions to reduce the interference or degradation and improves the overall stability of the topical composition. Encapsulation by the cross-linked silicone matrix may also alter the hydrophobicity/hydrophilicity of certain core particles that are intrinsically hydrophilic and allow such core particles to be formulated into oil or silicone phases that are typically incompatible with the un-encapsulated or "naked" hydrophilic particles. It is important to note that the desired chemical and/or physical properties of the core particles should remain substantially unaffected by the encapsulation described hereinabove.

Although applicable to any cosmetic or topical ingredient or component of solid, particulate form, it is believed that the present invention is particularly useful for stabilizing solid particles capable of causing generation of reactive oxygen species (ROS) without adversely affecting the desired properties of such particles. Reactive oxygen species (ROS), such as oxygen ions, free radicals, and peroxides (either inorganic or organic), are natural byproducts of the normal metabolism of oxygen by living cells. On one hand, ROS play important roles in cell signaling, a process termed redox signaling, and they are also used by the immune system to attack and kill pathogens, thereby protecting the living cells against invasion by such pathogens. On the other hand, ROS, if not reduced or eliminated timely, may cause extensive damage to all components of living cells, including proteins, lipids, and DNA. Thus, to maintain proper cellular homeostasis, a balance must be struck between the production and consumption of ROS. Various enzymes produced by the living cells, such as superoxide dismutase, catalase, and glutathione peroxidase, function as cellular antioxidants to eliminate the excess reactive oxygen species. Consequently, the ROS are present only at low levels in normal living cells, and the damage caused by them is constantly repaired by various cellular repair mechanisms. However, during times of environmental stress, the ROS levels can increase dramatically, which may lead to an imbalance between the production of ROS by a biological system and the biological system's capability to detoxify the reactive intermediates or repair the resulting damages. This cumulates into a situation commonly referred to as "oxidative stress." Oxidative stress is involved in many diseases, such as atherosclerosis, Parkinson's disease and Alzheimer's disease. Oxidative stress is also believed to be a major contributor to the aging process. Certain particles commonly used in cosmetic compositions, such as iron oxides, titanium dioxide, and zinc oxide, are known to cause generation of ROS, which not only can exert oxidative stress on the skin, but may also interfere with other ingredients or components in the cosmetic compositions. For example, many organic dyes/colorants, organic sunscreen agents, and other organic cosmetic ingredients are known to be susceptible to oxidative decomposition or degradation. Combined use of the ROS-releasing particles with such organic cosmetic ingredients may consequently lead to in situ decomposition or degradation of such organic cosmetic ingredients and adversely affect the overall performance and stability of the cosmetic compositions. Encapsulation of such ROS-releasing particles into the cross-linked silicone matrix of the present invention is believed to effectively eliminate or reduce any potential oxidative stress that such particles may exert on the skin, and to prevent such particles from causing the decomposition or degradation of other cosmetic ingredients. Consequently, the cross-linked silicone-encapsulated metal oxide particles of the present invention can be readily used with organic compounds that are known to be susceptible to oxidative decomposition or degradation to form topical or cosmetic compositions with significantly improved overall stability and prolonged shelf life.

The treated particles of the present invention can be added directly to any pharmaceutically or cosmetically acceptable carrier to form a cosmetic or topical composition. For purposes of the present invention, pharmaceutically or cosmetically acceptable carriers are substances that are biologically compatible with human skin and can be used to formulate active ingredients described hereinabove and/or hereinafter into a cream, gel, emulsion, liquid, suspension, powder, nail coating, skin oil, or lotion that can be topically applied. In the case where the cosmetically acceptable carrier is in the form of an emulsion, it may contain from about 0.1 to 99%, preferably from about 0.5 to 95%, more preferably from about 1 to 80% by weight of the total composition of water and from about 0.1 to 99%, preferably from about 0.1 to 80%, more preferably from about 0.5 to 75% by weight of the total composition of oil. In the case where the composition is anhydrous, it may comprise from about 0.1 to 90 wt % of oil and from about 0.1 to 75 wt % of other ingredients such as pigments, powders, non-aqueous solvents (such as mono-, di-, or polyhydric alcohols, etc. In the case where the composition is in the form of an aqueous based gel, solution, or suspension, it may comprise from about 0.1 to 99 wt % of water and from about 0.1 to 75 wt % of other ingredients such as botanicals, non-aqueous solvents, etc.

The pharmaceutically or cosmetically acceptable carrier or carriers can be present in the topical or cosmetic composition of the present invention at an amount ranging from about 0.1% to about 99.9%, preferably from about 5% to about 99.5%, more preferably from about 10% to about 99%, and most preferably from about 10% to 90% by total weight of the topical or cosmetic composition.

The topical or cosmetic composition may contain one or more skin care actives, which are agents that provide benefits to the skin, rather than merely improving the physical or aesthetic characteristics of the topical composition. If present, such skin care actives may range from about 0.01 to 50%, preferably from about 0.05 to 35% by weight of the total composition. Exemplary skin care additives that can be used in the topical or cosmetic compositions of the present invention include, but are not limited to: chemical or physical sunscreens, self-tanning agents such as dihydroxyacetone, anti-acne agents (e.g., resorcinol, salicylic acid, benzoyl peroxide, and the like), enzyme-inhibiting agents, collagen-stimulating agents, agents for the eradication of age spots and keratoses, analgesics, anesthetics, antimicrobials (e.g., antibacterials, antiyeast agents, antifungal agents, and antiviral agents), antidandruff agents, antidermatitis agents, antipruritic agents, antiemetics, anti-inflammatory agents, antihyperkeratolytic agents, antiperspirants, antipsoriatic agents, antiseborrheic agents, antihistamine agents, skin lightening agents, depigmenting agents, skin soothing/healing agents (e.g., aloe vera extract, allantoin, and the like), corticosteroids, hormones, proteins or peptides, vitamins and derivatives thereof (e.g., vitamin A, vitamin E, vitamin $B_3$, vitamin $B_5$, and the like), exfoliants, retinoids (e.g., retinoic acid and retinol), farnesol, bisabolol, phytantriol, glycerol, urea, guanidine (e.g., amino guanidine), clotrimazole, ketoconazole, miconozole, griseofulvin, hydroxyzine, diphenhydramine, pramoxine, lidocaine, procaine, mepivacaine, monobenzone, erythromycin, tetracycline, clindamycin, meclocyline, minocycline, hydroquinone, naproxen, ibuprofen, theophylline, cromolyn, albuterol, topical steroids (e.g., hydrocortisone, hydrocortisone 21-acetate, hydrocortisone 17-valerate, and hydrocortisone 17-butyrate), betamethasone valerate, betamethasone diproprionate, benzoyl peroxide, crotamiton, propranolol, promethazine, and mixtures or derivatives thereof. In a preferred, but not necessary embodiment of the present invention, the topical composition comprises one or more skin care actives selected from the group consisting of sunscreen agents, self-tanning agents, anti-aging agents, anti-wrinkle agents, anti-acne agents, antimicrobials, anti-inflammatory agents, skin-lightening agents, proteins or peptides, vitamins and derivatives thereof, exfoliants, ingredients that stimulate DNA repair, ingredients that provide immune protection, ingredients that stimulate cell renewal, ingredients that stimulate skin barrier repair, moisturizers, and mixtures thereof.

In a particularly preferred embodiment of the present invention, the topical or cosmetic composition is a sunscreen composition comprising treated particles containing core particles formed of zinc oxide, titanium dioxide, or both. As mentioned hereinabove, zinc oxide or titanium dioxide particles are known to have photoprotective characteristics and can therefore be used as physical sunscreen agents, but their uses in topical or cosmetic compositions are limited due to their photo-activity, i.e., their tendency to cause generation of reactive oxygen species upon exposure to UV light, which may degrade or otherwise interfere with certain organic cosmetic ingredients or skin care actives that are susceptible to oxidative decomposition or degradation. The encapsulation of zinc oxide and/or titanium dioxide particles as described in the present invention is believe to eliminate or reduce reactive oxygen species generated in the vicinity of such particles upon UV exposure, but without adversely affecting the sunscreen properties of such particles.

Consequently, the treated particles of the present invention containing zinc oxide and/or titanium dioxide can be readily formulated with organic cosmetic ingredients or skin care additives that are known to be susceptible to oxidative decomposition or degradation to form stable sunscreen compositions with significantly improved overall stability and prolonged shelf live. For example, the treated particles containing zinc oxide and/or titanium dioxide can be formulated with one or more organic dyes susceptible to oxidative decomposition or degradation to form color cosmetic compositions that also have sunscreen properties. For another example, the treated particles containing zinc oxide and/or titanium dioxide can be formulated with one or more organic sunscreen agents susceptible to oxidative decomposition or degradation, thereby forming sunscreen compositions that are not only characterized by high SPF values (e.g., SPF 30 or more), but also surprisingly and unexpectedly improved overall stability and prolonged shelf life. If present, such organic sunscreen agents may range from about 0.1 to 45% by weight of the total composition.

Exemplary organic sunscreen agents that can be used in combination with the $TiO_2$- and/or ZnO-containing treated particles of the present invention include, but are not limited to UVA and UVB sunscreens, such as benzophenones and derivatives thereof (e.g., benzophenone-3, dioxybenzone, sulisobenzone, octabenzone, hydroxy- and/or methoxy-substituted benzophenones, and benzophenonesulfonic acids and salts thereof); salicylic acid derivatives (e.g., ethylene glycol salicylate, triethanolamine salicylate, octyl salicylate, homomenthyl salicylate, and phenyl salicylate); urocanic acid and derivatives thereof (e.g., ethyl urocanate); p-aminobenzoic acid (PABA) and derivatives thereof (e.g., ethyl/isobutyl/glyceryl esters thereof and 2-ethylhexyl p-dimethylaminobenzoate, which is also referred to as octyldimethyl PABA); anthranilates and derivatives thereof (e.g., o-aminobenzoates and various esters of amino-benzoic acid); benzalmalonate derivatives; benzimidazole derivatives; imidazolines; bis-benzazolyl derivatives; dibenzoylmethanes and derivatives thereof (e.g., 4-tert-butyl-4'-methoxydibenzoylmethane, which is commonly referred to as "avobenzone," and 4-isopropyl-dibenzoylmethane); benzoazole/benzodiazole/benzotriazoles and derivatives thereof (e.g., 2-(2-hydroxy-5-methylphenyl)benzotriazole and methylene bis-benzotriazolyl tetramethylbutylphenol, which is commonly referred to as "Tinosorb M"); diphenylacrylates and derivatives thereof (e.g., 2-ethylhexyl-2-cyano-3,3-diphenylacrylate, which is commonly referred to as "octocrylene," and ethyl-2-cyano-3,3-diphenylacrylate, which is commonly referred to as "etocrylene"); diesters or polyesters containing diphenylmethylene or 9H-fluorene substitutional groups; 2-phenyl-benzimidazole-5-sulphonic acid (PBSA); 4,4-diarylbutadienes; cinnamates and derivatives thereof (e.g., 2-ethylhexyl-p-methoxycinnamate, octyl-p-methoxycinnamate, umbelliferone, methylumbelliferone, methylacetoumbelliferone, esculetin, methylesculetin, and daphnetin); camphors and derivatives thereof (e.g., 3-benzylidenecamphor, 4-methylbenzylidenecamphor, polyacrylamidomethyl benzylidenecamphor, benzylidene camphor sulfonic acid, and terephthalylidene dicamphor sulfonic acid, which is commonly referred to as "Encamsule"); triazines and derivatives thereof (e.g., 2,4-bis-{[4-(2-ethyl-hexyloxy)-2-hydroxy]-phenyl}-6-(4-methoxyphenyl)-1,3,5-triazine, which is commonly referred to as "Tinosorb S"); naphthalates and derivatives thereof (e.g., diethylhexyl-2,6-naphthalate); naphtholsulfonates and derivatives thereof (e.g., sodium salts of 2-naphthol-3,6-disulfonic and 2-naphthol-6,8-disulfonic acids); dibenzalacetone and benzalacetonephenone; diphenylbutadienes and derivatives thereof; di-hydroxynaphthoic acid and salts thereof; o- and p-hydroxybiphenyldisulfonates; coumarin derivatives (e.g., 7-hydroxy, 7-methyl, and 3-phenyl derivatives thereof); azoles/diazoles/triazoles and derivatives thereof (e.g., 2-acetyl-3-bromoindazole, phenyl benzoxazole, methyl naphthoxazole, and various aryl benzotriazoles); quinine and derivatives thereof (e.g., bisulfate, sulfate, chloride, oleate, and tannate salts thereof); quinoline and derivatives thereof (e.g., 2-phenylquinoline and 8-hydroxyquinoline salts); tannic acid and derivatives thereof (e.g., hexaethylether derivatives thereof); hydroquinone and derivatives thereof; uric acid and derivatives thereof; vilouric acid and derivatives thereof, and mixtures or combinations thereof. Salts and otherwise neutralized forms of certain acidic sunscreens from the list hereinabove are also useful herein. These organic sunscreen agents may be used alone or in combination of two or more. In addition, other known animal or vegetable extracts having UV light-absorbing ability may properly be used alone or in combination.

Organic sunscreen agents that are particularly useful for the practice of the present invention are: 4,4'-t-butyl methoxydibenzoylmethane, 2-ethylhexyl-2-cyano-3,3-diphenylacrylate, 2-ethylhexylsalicylate, 3,3,5-trimethylcyclohexylsalicylate, 2-ethylhexyl p-methoxycinnamate, 2-hydroxy-4-methoxybenzophenone, 2,2-dihydroxy-4-methoxybenzophenone, 2,4-bis-{4-(2-ethyl-hexyloxy)-2-hydroxy]-phenyl}-6-(4-methoxyphenyl)-1,3,5-triazine, methylene bis-benzotriazolyl tetramethylbutylphenol, terephthalylidene dicamphor sulfonic acid, diethylhexyl 2,6-naphthalate, digalloyltrioleate, ethyl 4-[bis(hydroxypropyl)] aminobenzoate, glycerol p-aminobenzoate, methylanthranilate, p-dimethylaminobenzoic acid or aminobenzoate, 2-ethylhexyl p-dimethylaminobenzoate, 2-phenylbenzimidazole-5-sulfonic acid, 2-(p-dimethylaminophenyl)-5-sulfoniobenzoxazoic acid, and mixtures or combinations thereof. Preferably, 4,4'-t-butyl methoxydibenzoylmethane is provided in the sunscreen compositions of the present invention, either with $TiO_2$-containing treated particles, or ZnO-containing treated particles, or both. More preferably, the sunscreen compositions of the present invention further include a second organic sunscreen agent selected from the lists provided hereinabove.

The cosmetically acceptable carrier may also contain one or more oils, which may be silicone, organic, or mixtures thereof. If present, such oils may range from about 0.1 to 99% by weight of the total composition and include volatile or non-volatile silicones such as cyclomethicone; methyl trimethicone; octamethyltrisiloxane; decamethyltetrasiloxane; dodecamethylpentasiloxane; dimethicone; phenyl trimethicone trimethylsiloxyphenyl dimethicone; phenyl dimethicone; cetyl dimethicone; dimethicone copolyol, cetyl dimethicone copolyol; glycerolated silicones such as lauryl PEG-9 polydimethylsiloxyethyl dimethicone; or mixtures thereof. Suitable esters include mono-, di-, or triesters of C4-30 fatty acids and mono-, di-, or polyhydric C1-20 alcohols, such as fatty acid (e.g., stearyl, behenyl, and isostearyl) esters of glycerin, or fatty acid esters of alpha hydroxyl acids such as citric, malic, or lactic acids and the like. Suitable hydrocarbons include monomeric or polymeric olefins or alpha olefins, such as polyisobutene, polydecene, polybutene, or hydrogenated derivatives thereof.

The cosmetically acceptable carrier may also comprise one or more humectants. If present, they may range from about 0.1 to 20% by weight of the total composition and include C1-4 alkylene glycols such as butylene, propylene, ethylene glycol, glycerin and the like.

The cosmetically acceptable carrier may also contain one or more waxes preferably having a melting point ranging from about 30 to 150° C. If present, such waxes may range from about 0.1 to 45% by weight of the total composition and include animal, vegetable, mineral, or silicone waxes. Examples include alkyl dimethicones stearyl dimethicone, candelilla, polyethylene, ozokerite, beeswax, and the like.

The cosmetically acceptable carrier may also comprise one or more organosiloxane elastomers, either emulsifying or non-emulsifying. If present, such elastomers may range from about 0.1 to 30% by weight of the total composition. Examples of suitable elastomers include dimethicone/vinyl dimethicone crosspolymer; dimethicone/dimethicone PEG/PPG 10/15 crosspolymer; and the like.

The cosmetically acceptable carrier may also include one or more pigments or powders or mixtures thereof. If present, the suggested range of such pigments or powders is from about 0.1 to 85% by weight of the total composition. The particle sizes of such pigments or powders may range from about 0.05 to 200 microns but are preferably about 50-100 microns. Examples of pigments include organic pigments such as D&C or FD&C colors or Lakes thereof including blues, browns, reds, etc; or inorganic iron oxides such as brown, yellow, green, red, iron oxides. Suitable powders include titanium dioxide, nylon, PMMA, boron nitride, mica, and the like.

The cosmetically acceptable carrier may also comprise one or more nonionic surfactants, particularly if the topical or cosmetic composition of the present invention is provided in the emulsion form. If present, such surfactants may range from about 0.1 to 20% by weight of the total composition. Suitable surfactants include ethoxylated fatty C6-30 alcohols such as steareth, beheneth, ceteth where the number following each of the surfactants refers to the number of repeating ethylene oxide groups which may range from 2 to 250, e.g. steareth-2, beheth-30 and so on.

The present invention can be further illustrated in the following non-limiting examples.

Example I

TiO$_2$ particles were first coated with Gantrez S-97BF polymer and then with KF9909 silicone fluid under sonication, and the coated particles were then mixed with more KF9909 silicone fluid in a main beaker and mixed together using a pro mixer manufactured by Caframo in Ontario, Canada (Model # BDC 1850) at digital reading of 105 until a homogenous mixture was formed. Stannous octoate, which was commercially available from Arkema as Fascat® 2003 catalyst, was added into the main beaker at room temperature, and mixing was resumed for about 1 minute. The resulting mixture was immediate poured onto a flat surface and allowed to sit for 30 minutes, thereby forming a cross-linked flat sheet. The flat sheet was subsequently reduced to particles by mortar pestle. The resulting treated particles had an average particle size ranging from about 1 micron to 10 microns, as measured under microscope. Such treated particles contained about 85.31 wt % of TiO$_2$, 3.52% Gantrez S-97BF, 0.41% stannous octoate, and about 12.57 wt % of KF-9909 silicone fluid.

While the present invention has been described hereinabove with reference to specific embodiments, features and aspects, it will be recognized that the invention is not thus limited, but rather extends in utility to other modifications, variations, applications, and embodiments, and accordingly all such other modifications, variations, applications, and embodiments are to be regarded as being within the spirit and scope of the present invention.

What I claim is:

1. A topical composition comprising a dispersion of treated particles in a cosmetically or pharmaceutically acceptable carrier, wherein each of said treated particles comprises one or more core particles encapsulated in a cross-linked silicone matrix, and wherein each of the treated particles possesses an electrical potential in the range of from about −40 mV to about −80 mV.

2. The composition of claim 1, wherein the treated particles have an average particle size ranging from about 1 micron to about 50 microns, and the core particles have an average particle size ranging from about 0.001 micron to about 0.5 micron.

3. The composition of claim 1, wherein the cross-linked silicone matrix is formed by cross-linking a silicone having branched reactive alkoxyl moieties.

4. The composition of claim 3, wherein the branched reactive moieties comprise ethoxy or ethoxysilylethyl groups.

5. The composition of claim 3, wherein the cross-linked silicone matrix is formed by cross-linking triethoxysilylethyl polydimethylsiloxyethyl hexyl dimethicone.

6. The composition of claim 1, wherein the core particles comprise one or more metal oxides.

7. The composition of claim 6, wherein the core particles comprises titanium dioxide, zinc oxide, or a combination thereof.

8. The composition of claim 6, further comprising at least one organic compound susceptible to oxidative decomposition or degradation.

9. The composition of claim 8, wherein said organic compound is an organic sunscreen agent susceptible to oxidative decomposition or degradation.

10. The composition of claim 9, wherein the organic sunscreen agent is 4,4'-t-butyl methoxydibenzoylmethane.

11. The composition of claim 8, wherein said organic compound is an organic dye susceptible to oxidative decomposition or degradation.

12. The composition of claim 1, wherein each of the core particles is first coated by an inner layer of an anionic polymer selected from the group consisting of acrylates copolymers and methyl vinyl ether and maleic anhydride (PVM/MA) copolymers, and then encapsulated into the cross-linked silicone matrix.

13. The composition of claim 12, wherein the anionic polymer possesses an electrical potential ranging from about −10 mV to about −100 mV.

14. The composition of claim 12, wherein the anionic polymer possesses an electrical potential ranging from about −30 mV to about −80 mV.

15. The composition of claim 12, wherein the core particles have a density that is larger than the densities of the anionic polymer and the silicone, and wherein the anionic polymer has a density that is larger than that of the silicone.

16. A treated particle comprising one or more core particles encapsulated in a cross-linked silicone matrix, wherein said treated particle has a particle size ranging from about 1 micron to about 50 microns, and an electrical potential ranging from about −40 mV to about −80 mV.

17. A treated particle of claim 16, wherein the one or more core particles comprise one or more metal oxides selected from the group consisting of titanium dioxide and zinc oxide.

18. The treated particle of claim 16, wherein each of the one or more core particles is first coated by an inner layer of an anionic polymer, and then encapsulated into the cross-linked silicone matrix.

19. A method for forming treated particles, comprising:
(a) Coating one or more core particles having an average particle size ranging from about 0.001 micron to about 0.5 micron with an anionic copolymer selected from the group consisting of acrylates copolymers and methyl vinyl ether maleic anhydride (PVM/MA) copolymers;
(b) coating the coated particles of (a) with silicone;
(c) contacting the coated particles of (b) with a cross-linking agent, wherein the cross-linking agent comprises a stannous carboxylate capable of effectuating cross-linking of the silicone coating, thereby forming a cross-linked structure with the core particles encapsulated therein; and (d) reducing the cross-linked structure into treated particles having an average particle size ranging from about 1 micron to about 50 microns and an electrical potential ranging from about −40 mV to about −80 mV, wherein each of the treated particles comprises one or more of said core particles encapsulated in a cross-linked silicone matrix.

20. The method of claim 19, wherein the silicone is triethoxysilylethyl polydimethylsiloxyethyl hexyl dimethicone, wherein the stannous carboxylate is stannous octoate, and wherein cross-linking of the silicone coating is effectuated at room temperature with continuous mixing.

* * * * *